US011324687B2

(12) United States Patent
Peschard et al.

(10) Patent No.: US 11,324,687 B2
(45) Date of Patent: May 10, 2022

(54) PRO-PIGMENTING PEPTIDES

(71) Applicant: Sederma, Le Perray en Yvelines (FR)

(72) Inventors: Olivier Peschard, Saint Prest (FR); Philippe Mondon, Montrouge (FR)

(73) Assignee: Sederma

( * ) Notice: Subject to any disclaimer, the term of this patent is extended or adjusted under 35 U.S.C. 154(b) by 32 days.

(21) Appl. No.: 16/848,142

(22) Filed: Apr. 14, 2020

(65) Prior Publication Data

US 2020/0253852 A1 Aug. 13, 2020

Related U.S. Application Data

(62) Division of application No. 16/259,176, filed on Jan. 28, 2019, now Pat. No. 10,660,839, which is a division of application No. 15/361,801, filed on Nov. 28, 2016, now Pat. No. 10,231,917, which is a division of application No. 14/646,999, filed as application No. PCT/IB2013/060390 on Nov. 25, 2013, now Pat. No. 9,534,015.

(30) Foreign Application Priority Data

Nov. 26, 2012 (FR) ...................................... 1261205

(51) Int. Cl.
| | |
|---|---|
| *C07K 5/103* | (2006.01) |
| *C07K 5/093* | (2006.01) |
| *C07K 5/087* | (2006.01) |
| *C07K 5/097* | (2006.01) |
| *C07K 5/078* | (2006.01) |
| *C07K 5/062* | (2006.01) |
| *A61K 38/00* | (2006.01) |
| *A61Q 19/02* | (2006.01) |
| *A61K 8/64* | (2006.01) |
| *A61Q 5/10* | (2006.01) |
| *A61Q 19/04* | (2006.01) |
| *A61Q 19/08* | (2006.01) |
| *C07K 5/083* | (2006.01) |
| *A61Q 19/00* | (2006.01) |

(52) U.S. Cl.
CPC .................. *A61K 8/64* (2013.01); *A61Q 5/10* (2013.01); *A61Q 19/007* (2013.01); *A61Q 19/04* (2013.01); *A61Q 19/08* (2013.01); *C07K 5/06026* (2013.01); *C07K 5/06165* (2013.01); *C07K 5/081* (2013.01); *C07K 5/0806* (2013.01); *C07K 5/0808* (2013.01); *C07K 5/0812* (2013.01); *C07K 5/0819* (2013.01); *C07K 5/0821* (2013.01); *C07K 5/1008* (2013.01); *A61K 38/00* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 4,687,840 A | 8/1987 | Pang et al. | |
| 4,772,587 A | * 9/1988 | Tanaka | .................. C07D 207/08 |
| | | | 514/17.7 |
| 8,097,590 B2 | 1/2012 | Pinel et al. | |
| 8,450,456 B2 | 5/2013 | Dal Farra et al. | |
| 2007/0231284 A1 | 10/2007 | Pinel et al. | |
| 2010/0261658 A1 | 10/2010 | Dal Farra et al. | |
| 2011/0092431 A1 | 4/2011 | Ohsawa et al. | |

FOREIGN PATENT DOCUMENTS

| | | | | |
|---|---|---|---|---|
| CN | 101538236 | * | 9/2009 | ............. A01N 25/00 |
| EP | 2049074 B1 | | 7/2010 | |
| FR | 2702766 A1 | | 9/1994 | |
| FR | 2788777 A1 | | 7/2000 | |
| WO | 98/07744 A1 | | 2/1998 | |
| WO | 00/58347 A1 | | 10/2000 | |
| WO | 02/066668 A2 | | 8/2002 | |
| WO | 03/017966 A2 | | 3/2003 | |
| WO | 2004012650 A2 | | 2/2004 | |

(Continued)

OTHER PUBLICATIONS

Antohi et al., "Ab initio calculations on blocked Pro-Ala dipeptides," Journal of molecular structure 430: 247-258 (1998) (Year: 1998).*
Liang et al., Thermodynamic Analysis of /3-Turn Formation in Pro-Ala, Pro-Gly, and Pro-Val Model Peptides in Methylene Chloride, J. Am. Chem. Soc. 114:4440-4442 (1992) (Year: 1992).*
Renard et al., "Hydrolysis of Pro-Ala Dipeptides by Lysosomal Hydrolases. Models for the Study of Lysosomotropic Amino Acid Prodrugs of Penicillins," J. Med. Chem. 29: 1291-1293 (1986) (Year: 1986).*

(Continued)

*Primary Examiner* — Julie Ha
*Assistant Examiner* — Kristina M Hellman
(74) *Attorney, Agent, or Firm* — Lerner, David, Littenberg, Krumholz & Mentlik, LLP

(57) ABSTRACT

Provided is at least one peptide of formula (I) and its use, where formula (I) is as follows: X-$(Xaa_1)_n$-Pro*-$(Xaa_2)_m$-Y (I). In formula (I), n=0 and m=1. At the N terminal end of the peptide, X is selected from H, —CO—$R_1$ and —$SO_2$—$R_1$. At the C terminal end of the peptide, Y is selected from OH, $OR_1$, $NH_2$, $NHR_1$ or $NR_1R_2$, $R_1$ and $R_2$ being independently selected from an alkyle, aryle, aralkyle, alkylaryl, alkoxy and aryloxy group, that can be linear, branched, cyclic, poly-cyclic, non-saturated, hydroxylated, carbonylated, phosphorylated and/or sulphured, with the possibility to have in said group skeleton a O, S and/or N heteroatom. Pro* corresponds to a Proline, an analogue or derivative thereof.

3 Claims, No Drawings

Specification includes a Sequence Listing.

(56) References Cited

FOREIGN PATENT DOCUMENTS

| WO | 2004024695 | A1 | 3/2004 |
|----|-----------|----|--------|
| WO | 2006120646 | A1 | 11/2006 |
| WO | 2008009709 | A1 | 1/2008 |
| WO | 2008059127 | A1 | 5/2008 |
| WO | 2009104118 | A1 | 8/2009 |
| WO | 2010067327 | A1 | 6/2010 |
| WO | 2010082175 | A2 | 7/2010 |
| WO | 2010082176 | A2 | 7/2010 |
| WO | 2011086532 | A1 | 7/2011 |
| WO | 2011125039 | A2 | 10/2011 |
| WO | 2012104774 | A1 | 8/2012 |
| WO | 2013046137 | A2 | 4/2013 |
| WO | 2013105047 | A2 | 7/2013 |
| WO | 2013105048 | A2 | 7/2013 |

OTHER PUBLICATIONS

Mhaskar et al., "Synthesis of Diethanolamides of N-Lauroyl Dipeptides and Correlation of Their Structures with Surfactant and Antibacterial Properties," JAOCS 69:643-646 (1992) (Year: 1992).*

Grassert et al., "Amphiphilic Proline and Prolylproline Derivatives in the Rhodium(I)-Catalyzed Asymmetric Hydrogenation in Water: Chiral Induction as Indication of the Location of reactants within the micelle," Chirality 10:754-759 (1998) (Year: 1998).*

Nakamura et al., "the macromolecular films of n-palmityoyl-L-proline oligomers," Journal of colloid and interface science 61:86-94 (1977) (Year: 1977).*

Crisma et al., "confirmation characteristics of the—Pro-Ala—the peptide sequence," Zeitschrift für Kristallographie 212:465-471 (1997) (Year: 1997).*

Andersson et al., "Glycine-Amide is an Active Metabolite of the Antiretroviral Tripeptide Glycyl-Prolyl-Glycine-Amide," Antimicrob. Agents Chemotherapy 49:40-44 (2005).

International Search Report and Written Opinion for Application No. PCT/IB2013/060390 dated Aug. 11, 2014.

Knipe, Reactions of Aldehydes and Ketones and their Derivatives, Organic Reaction Mechanisms 2007: An annual survey covering the literature dated Jan. to Dec. 2007, Chapter 1, pp. 1-45, 2007.

Marye Anne Fox et al: "Electric Field Effects on Electron Transfer Rates in Dichromophoric Peptides: The Effect of Helix Unfolding", Journal of the American Chemical Society, vol. 119, No. 23, Jun. 1, 1997 (Jun. 1, 1997), pp. 5277-5285 , XP055132476.

The Scientific Committee on Consumer Safety SCCS, "The SCCS's Notes of Guidance for the testing of cosmetic substances and their safety evaluation 8th Revision", Dec. 11, 2012.

Vernaleken et al., "Tripeptides of RS1 (RSC1A1) Inhibit a Monosaccharide-dependent Exocytotic Pathway of Na+-D-Glucose Cotransporter SGLT1 with High Affinity," J. Biol. Chem. 282:28501-28513 (2007).

Zhang et al., Converting peptides into drug leads by lipidation, Medicinal Chemistry, vol. 19, Issue 11, pp. 1602-1618, Apr. 2012.

* cited by examiner

```
                         SEQUENCE LISTING

<160> NUMBER OF SEQ ID NOS: 16

<210> SEQ ID NO 1
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is H, -CO-R1 or -SO2-R1, R1 being an alkyle,
      aryle, aralkyle, alkylaryle, alkoxy or aryloxy group that can be
      linear, branched, (poly)cyclic, unsaturated, hydroxylated,
      carbonylated, phosphorylated and/or sulfured, containing or not an
      O, S and/or
<220> FEATURE:
<221> NAME/KEY: MOD_RES
<222> LOCATION: (4)..(4)
<223> OTHER INFORMATION: Y is OH, OR1, NH2, NHR1 or NR1R2;  R1, R2 being
      an alkyle, aryle, aralkyle, alkylaryle, alkoxy or aryloxy group
      that can be linear, branched, (poly)cyclic, unsaturated,
      hydroxylated, carbonylated, phosphorylated and/or sulfured,
      containing or not an O, S or N.

<400> SEQUENCE: 1

Ala Gln Pro Arg
1

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X is H, -CO-R1 or -SO2-R1, R1 being an alkyle,
      aryle, aralkyle, alkylaryle, alkoxy or aryloxy group that can be
      linear, branched, (poly)cyclic, unsaturated, hydroxylated,
      carbonylated, phosphorylated and/or sulfured, containing or not an
      O, S and/or
<220> FEATURE:
<221> NAME/KEY: MOD_RES
<222> LOCATION: (4)..(4)
<223> OTHER INFORMATION: Y is OH, OR1, NH2, NHR1 or NR1R2;  R1, R2 being
      an alkyle, aryle, aralkyle, alkylaryle, alkoxy or aryloxy group
      that can be linear, branched, (poly)cyclic, unsaturated,
      hydroxylated, carbonylated, phosphorylated and/or sulfured,
      containing or not an O, S or N.
```

<400> SEQUENCE: 2

Ala Gln Pro Lys
1

<210> SEQ ID NO 3
<211> LENGTH: 4
<212> TYPE: PRT
<213> ORGANISM: artificial sequence
<220> FEATURE:
<223> OTHER INFORMATION: synthetic peptide

<400> SEQUENCE: 3

Arg Ser Arg Lys
1

<210> SEQ ID NO 4
<211> LENGTH: 4
<212> TYPE: PRT
<213> ORGANISM: artificial sequence
<220> FEATURE:
<223> OTHER INFORMATION: synthetic peptide

<400> SEQUENCE: 4

Gly Gln Pro Arg
1

<210> SEQ ID NO 5
<211> LENGTH: 4
<212> TYPE: PRT
<213> ORGANISM: artificial sequence
<220> FEATURE:
<223> OTHER INFORMATION: synthetic peptide

<400> SEQUENCE: 5

Lys Thr Phe Lys
1

<210> SEQ ID NO 6
<211> LENGTH: 5
<212> TYPE: PRT
<213> ORGANISM: artificial sequence
<220> FEATURE:
<223> OTHER INFORMATION: synthetic peptide

<400> SEQUENCE: 6

Lys Thr Thr Lys Ser
1               5

<210> SEQ ID NO 7
<211> LENGTH: 6
<212> TYPE: PRT
<213> ORGANISM: artificial sequence
<220> FEATURE:
<223> OTHER INFORMATION: Synthetic peptide

<400> SEQUENCE: 7

Gly Lys Thr Thr Lys Ser
1               5

<210> SEQ ID NO 8
<211> LENGTH: 6
<212> TYPE: PRT
<213> ORGANISM: artificial sequence
<220> FEATURE:
<223> OTHER INFORMATION: synthetic peptide

```
<400> SEQUENCE: 8

Val Gly Val Ala Pro Gly
1               5

<210> SEQ ID NO 9
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 9

Gly Gln Pro Arg
1

<210> SEQ ID NO 10
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by an Elaidoyl chain

<400> SEQUENCE: 10

Lys Thr Phe Lys
1

<210> SEQ ID NO 11
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 11

Lys Thr Thr Lys Ser
1               5

<210> SEQ ID NO 12
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain
<220> FEATURE:
<221> NAME/KEY: misc_feature
<222> LOCATION: (5)..(5)
<223> OTHER INFORMATION: Xaa can be any naturally occurring amino acid

<400> SEQUENCE: 12

Tyr Gly Gly Phe Xaa
1               5

<210> SEQ ID NO 13
```

```
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 13

Val Gly Val Ala Pro Gly
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 14

Gly Lys Thr Thr Lys Ser
1               5

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 15

Ala Gln Pro Arg
1

<210> SEQ ID NO 16
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 16

Ala Gln Pro Lys
1
```

PRO-PIGMENTING PEPTIDES

CROSS-REFERENCE TO RELATED APPLICATIONS

The present application is a divisional application of U.S. patent application Ser. No. 16/259,176 filed on Jan. 28, 2019, which is a divisional of U.S. patent application Ser. No. 15/361,801 filed on Nov. 28, 2016, which is a divisional of U.S. patent application Ser. No. 14/646,999 filed on May 22, 2015, now U.S. Pat. No. 9,534,015, which application is a national phase entry under 35 U.S.C. § 371 of International Application No. PCT/IB2013/060390 filed Nov. 25, 2013, published in English, which claims priority from French Patent Application No. 1261205 filed Nov. 26, 2012, all of which are hereby incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 24, 2013, is named PALPA PCT_ST25 (3) and is 4.68 kilobytes in size.

TECHNICAL FIELD

The present invention relates to peptides for the treatment of skin and its appendages of mammals, humans or animals, and more particularly peptides for a cosmetic pro-pigmenting treatment.

The invention concerns the industries of cosmetics, hygiene and personal care, cosmeceutics and dermocosmetic products.

Peptides have an important signal function and coordinate many biochemical processes. Therefore they became essential and promising active ingredients especially in the cosmetics industry where compounds are constantly sought that can beautify the skin and its appendages, i.e. to improve their general condition.

The present inventors are particularly interested in search of new peptides with pro-pigmenting activity, especially at low levels, and peptides having in addition a procollagen activity in order to propose peptides that can have a pro-pigmenting and pro-collagen dual activity.

A pro-pigmenting active will act mainly on the stimulation of melanin synthesis (melanogenesis), the natural pigment of the skin, body hair, eyelashes, and hair, so as to intensify the normal pigmentation of the skin and appendages without solar or UV radiations. It is the melanocytes located in the epidermis that will produce melanin from the tyrosine amino acid. Tyrosinase and then other enzymes take place to convert tyrosine and to form melanin.

Applications include the repigmentation of cutaneous white spots and acceleration and intensification of tanning. A pro-pigmenting active can also be used for prevention and repigmentation of hair, body hair, eyelashes, eyebrows (canity treatment). Applications can be for a cosmetic or dermatological purposes, preventive or curative, for example a self-tanning treatment or a treatment for improving complexion uniformity, a treatment to strengthen the phototype of a person with a light and sun-sensitive skin, a treatment to prepare the skin before sun exposure, a treatment of white spots in particular due to a partial melanocytic deficit.

BACKGROUND ART

Dihydroxyacetone, also known as DHA or 1, 3-dihydroxy-2-propanone, is a well known pro-pigmenting active.

In cosmetics, tanning agents called TYR-OL™ and TYR-EXCEL™ proposed by Sederma and described respectively in FR2702766 and WO03/017966 based on Oleyl Tyrosine are also known.

EP2049074 describes the use of a rice protein hydrolyzate as a pigmenting active. The hydrolyzate is characterized in that it comprises a mixture of peptides in which at least 50% have a molecular weight preferably between 300 and 3500 Da, that is to say, from 3 to about 30 amino acids. Almost all naturally occurring amino acids are found in the hydrolyzate.

Besides, many peptides are disclosed for anti-age or anti-aging activity by stimulating the proteins of dermal extracellular matrix. For example, FR 2788777 patent describes PR-OH and Pal-PR-OH peptides in anti-aging cosmetic compositions.

SUMMARY OF THE INVENTION

The first object of the present invention is the directed to the use of at least one peptide of formula:

$$X\text{-}(Xaa_1)_n\text{-}Pro^*\text{-}(Xaa_2)_m\text{-}Y \qquad (I)$$

With:
n=0, 1 or 2;
m=0 or 1 and if m=0 then n 0
$Xaa_1$ is:
An hydrophobic amino acid selected from Alanine (Ala, A), Valine (Val, V), Methionine (Met, M), Leucine (Leu, L), Isoleucine (Ile, I), Phenylalanine (Phe, F), Proline (Pro, P) and analogues and derivatives thereof;
A polar amino acid selected from Serine (Ser, S), Threonine (Thr, T), Tyrosine (Tyr, Y), Asparagine (Asn, N), Glutamine (Gln, Q) and analogues and derivatives thereof; or
Glycine (Gly, G);
When n=2 the two amino acids $Xaa_1$ can be the same or different;
$Xaa_2$ is:
An hydrophobic amino acid selected from Alanine (Ala, A), Valine (Val, V), Methionine (Met, M), Leucine (Leu, L), Isoleucine (Ile, I), Phenylalanine (Phe, F), Proline (Pro, P) and analogues and derivatives thereof;
A basic amino acid selected from Arginine (Arg, R), Lysine (Lys, K) and Histidine (His, H) and analogues and derivatives thereof;
Glycine (Gly, G) or Serine (Ser, S);
At the N terminal end of the peptide, X is selected from H, —CO—$R_1$ and —$SO_2$—$R_1$;
At the C terminal end of the peptide, Y is selected from OH, $OR_1$, $NH_2$, $NHR_1$ or $NR_1R_2$,
$R_1$ and $R_2$ being independently from each other, selected from an alkyle, aryle, aralkyle, alkylaryl, alkoxy and aryloxy group, that can be linear, branched, cyclic, poly-cyclic, non-saturated, hydroxylated, carbonylated, phosphorylated and/or sulphured, with the possibility to have in said group skeleton a O, S and/or N heteroatom;
Pro* corresponding to a Proline, an analogue or derivative thereof;
Excluding the peptides where X=H and Y=OH,
For a non therapeutical cosmetic pro-pigmenting treatment of skin.

The inventors have shown that such peptides have a cosmetic activity and can be used individually or in combination to improve the appearance and general condition of the skin and its appendages, and in particular for the treatment and/or prevention of signs of aging and/or imperfections of skin and its appendages, in particular thanks to a pro-pigmenting activity.

More particularly, according to the invention a pro-pigmenting cosmetic use comprises the repigmentation of cutaneous white spots and acceleration and intensification of tanning, prevention and repigmentation of hair, body hair, eyelashes, eyebrows (canity treatment), self-tanning treatment or a treatment for improving complexion uniformity, a treatment to strengthen the phototype of a person with a light and sun-sensitive skin, a treatment to prepare the skin before sun exposure or a treatment of white spots in particular due to a partial melanocytic deficit.

The peptides of the invention advantageously have a pro-pigmenting activity even at in low ppm content, around 3 ppm for some of them, and in any case below 20 ppm. The presence of a proline (or pyrrolidine-2-carboxylic acid, the following formula II) is an essential element of the invention. It induces a strong geometrical constraint on the peptide skeleton. This configuration forces a "angled" shape (or as a hook) to the peptide. If the proline is substituted by a more flexible amino acid such as a glycine the pro-pigmenting activity disappears.

Formula II

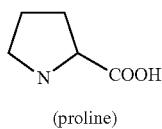

(proline)

The following developed formula III of the peptide Pal-LPA-OH according to the invention illustrates as an example this angled structure:

Formula III

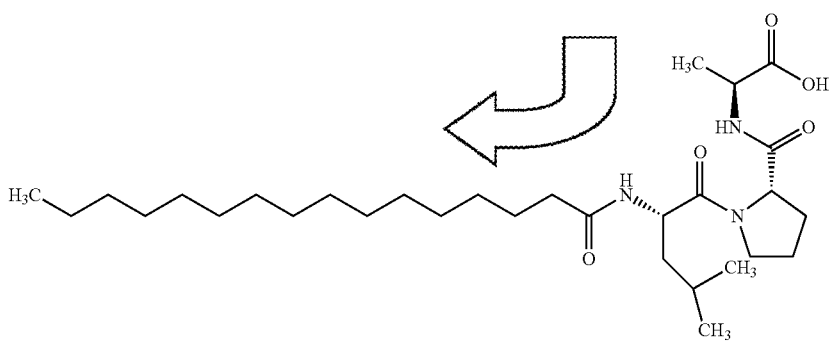

The present invention also encompasses proline derivatives or analogues that are also capable to induce such a bend. These derivatives or analogues are either:

1) Derived from rings of different size (e.g. 4 or 6 bonds);

2) Derived from the change in the relative position (α or β) of the acid function (COOH) with respect to the nitrogen-containing cycle.

3) Derived from substitutions on the cycle changing its overall size and/or its polarity.

4) Derived from the combination of the above items.

The peptides can be represented by the following general formula IV:

In either position

Formula IV

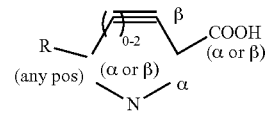

The present invention preferably provides the following analogues presented in the following Table 1 with a nitrogen in the ring as the proline (5 atoms cycle and COOH in α):

| Compound name | Chemical structure |
| --- | --- |
| azetidine-2-carboxylic acid | 4 atoms cycle and COOH in α |
| β-proline (or pyrrolidine-3-carboxylic acid) | 5 atoms cycle and COOH in β |
| pipecolic acid | 6 atoms cycle and COOH in α |
| nipecotic acid | 6 atoms cycle and COOH in β |
| thio-proline (or thiazolidine-4-carboxylic acid) | 5 atoms cycle and COOH in α + S in position 4 |
| 4-hydroxy-proline | 5 atoms cycle and COOH in α + OH in position 4 |
| 3,4-dehydro-proline | 5 atoms cycle and COOH in α + insaturation in 3-4 |

Other compounds resulting from the substitution of proline with a R group are also possible. Non-limiting examples are given in Table 2:

| R group | Position |
| --- | --- |
| piperidin-4-yl | 1 on nitrogen |
| phenyl; dimethyl | 3 |
| phenyl; OH; NH$_2$; F; F$_2$; CF$_3$; benzyl; cyclohexyl; oxo; bromobenzyl; SH; | 4 |

-continued

| R group | Position |
| --- | --- |
| phenoxy | |
| phenyl; dimethyl; oxo | 5 |
| phenyl, cyclohexyl | 4 + 5 |

Proline can also be replaced by substituted analogues having a 6 link cycle as the examples given in following Table 3:

| Compound name | Chemical structure |
| --- | --- |
| 3-carboxy-morpholine | 6 atoms cycle oxygenated + COOH in position 3 |
| 2-carboxy-morpholine | 6 atoms cycle oxygenated + COOH in position 2 |
| Tic (or 1,2,3,4-tétrahydroisoquinoline-3-carboxylic acid) and its hydroxylated derivative | 6 atoms cycle oxygenated + COOH in position 2 on this cycle + phenyl in position 4 + 5 |
| Tiq (or 1,2,3,4-tetrahydroisoquinoline-1-carboxylic acid) | 6 atom cycle + COOH in position 6 sur on this cycle + indole in position 4 + 5 |

According to the invention, preferably in formula I:
Pro* is Proline, a natural amino acid; and/or
$Xaa_1$ is selected from Alanine (Ala, A), Methionine (Met, M), Leucine (Leu, L), Isoleucine (Ile, I), Proline (Pro, P), Serine (Ser, S), Tyrosine (Tyr, Y) and Glutamine (Gln, Q); and more preferably selected from Leucine (Leu, L), Proline (Pro, P), Serine (Ser, S) and Glutamine (Gln, Q), and/or
$Xaa_2$ is selected from Alanine (Ala, A), Arginine (Arg, R), Methionine (Met, M), Glycine (Gly, G) and Serine (Ser, S).

As shown in examples given below in the detailed description, better results in pro-pigmentation can be obtained with these preferred amino-acids.

According to other features of the invention, preferably n=1 and m=0, or n=0 and m=1, in order to provide dipeptides, or n=2 and m=0, or n=1 and m=1, in order to provide tripeptides, dipeptides and tripeptides being easier and less expensive to synthesize.

Thus, proline based dipeptides covered by the invention can be selected from:
If n=0 and m=1: the general formula is then: X-Pro-$Xaa_2$-Y (formula V):
X-PA-Y, X-PV-Y, X-PM-Y, X-PL-Y, X-PI-Y, X-PF-Y, X-PP-Y, X-PR-Y, X-PK-Y, X-PH-Y, X-PG-Y and X-PS-Y, and more preferably X-PA-Y, X-PR-Y, X-PM-Y, X-PG-Y and X-PS-Y, according to the above mentioned preferred $Xaa_2$ amino acids.

If n=1 and m=0: the general formula is then: X-$Xaa_1$-Pro-Y (formula VI):
X-AP-Y, X-VP-Y, X-MP-Y, X-LP-Y, X-IP-Y, X-FP-Y, X-PP-Y, X-SP-Y, X-TP-Y, X-YP-Y, X-NP-Y, X-QP-Y and X-GP-Y, and preferably X-AP-Y, X-MP-Y, X-LP-Y, X-IP-Y, X-PP-Y, X-SP-Y, X-YP-Y and X-QP-Y, and more preferably X-LP-Y, X-PP-Y, X-SP-Y and X-QP-Y, according to the above mentioned preferred $Xaa_1$ amino acids.

The preferred dipeptides according to the invention are thus the X-PA-Y, X-PR-Y, X-PM-Y, X-PG-Y, X-PS-Y, X-LP-Y, X-PP-Y, X-SP-Y and X-QP-Y.

Tripeptides covered according to the invention based on proline can in turn be selected from:
If n=1 and m=1, the general formula is then: X-$Xaa_1$-Pro-$Xaa_2$-Y (formula VII):
Preferably, according to the above mentioned preferred amino-acids, the tripeptides of formula VII are selected from: X-APA-Y, X-APR-Y, X-APM-Y, X-APG-Y, X-APS-Y, X-MPA-Y, X-MPR-Y, X-MPM-Y, X-MPG-Y, X-MPS-Y, X-LPA-Y, X-LPR-Y, X-LPM-Y, X-LPG-Y, X-LPS-Y, X-IPA-Y, X-IPR-Y, X-IPM-Y, X-IPG-Y, X-IPS-Y, X-PPA-Y, X-PPR-Y, X-PPM-Y, X-PPG-Y, X-PPS-Y, X-SPA-Y, X-SPR-Y, X-SPM-Y, X-SPG-Y, X-SPS-Y, X-YPA-Y, X-YPR-Y, X-YPM-Y, X-YPG-Y, X-YPS-Y, X-QPA-Y, X-QPR-Y, X-QPM-Y, X-QPG-Y, X-QPS-Y, X-GPA-Y, X-GPR-Y, X-GPM-Y, X-GPG-Y and X-GPS-Y.

Even more preferably the tripeptides of formula VII are selected from: X-LPA-Y, X-LPR-Y, X-LPM-Y, X-LPG-Y, X-LPS-Y, X-PPA-Y, X-PPR-Y, X-PPM-Y, X-PPG-Y, X-PPS-Y, X-SPA-Y, X-SPR-Y, X-SPM-Y, X-SPG-Y, X-SPS-Y, X-QPA-Y, X-QPR-Y, X-QPM-Y, X-QPG-Y and X-QPS-Y.

As preferred examples of tetrapeptides, responding to the formula X-$Xaa_1$-$Xaa_1$-P-$Xaa_2$-Y (formula VIII) with n=2 and m=1, the following can be cited X-AQPR-Y (SEQ ID NO: 1) and X-AQPK-Y (SEQ ID NO: 2).

The inventors have shown that the peptides according to the invention have a pro-pigmenting activity as well as for some of them an additional stimulatory activity of collagen synthesis, advantageously providing an active with a dual activity, pro-pigmenting and pro-collagen, activity particularly interesting in particular for a anti-aging goal (treatment of spots and wrinkles with the same active).

This is the case in particular for the following peptides X-SPR-Y, X-PPR-Y, X-QPA-Y, X-LPA-Y, X-SPA-Y, X-PM-Y, and X-PA-Y, as can be seen in the detailed examples given below.

Advantageously also, some of the peptides present a keratinocyte differentiation property which allows to consider an additional activity at the epiderm level (moisturizing, strengthening the skin barrier). This activity also complements a global anti-aging activity.

This is the case in particular for the following peptides X-LPR-Y, X-SPR-Y, X-PA-Y and X-LPA-Y, as can be seen also in the detailed examples.

As a second subject matter the present invention proposes the following new peptides, suitable for a cosmetic treatment in particular a pro-pigmenting treatment, of formula:

$$X\text{-}(Xaa_1)_n\text{-}Pro^*\text{-}(Xaa_2)_m\text{-}Y \qquad (I)$$

With:
n=1 or 2;
m=1;
$Xaa_1$ is:
An hydrophobic amino acid selected from Alanine (Ala, A), Valine (Val, V), Methionine (Met, M), Leucine (Leu, L), Isoleucine (Ile, I), Phenylalanine (Phe, F), Proline (Pro, P) and analogues and derivatives thereof;
A polar amino acid selected from Serine (Ser, S), Threonine (Thr, T), Tyrosine (Tyr, Y), Asparagine (Asn, N), Glutamine (Gln, Q) and analogues and derivatives thereof; or
Glycine (Gly, G);
When n=2 the two amino acids $Xaa_1$ can be the same or different;
$Xaa_2$ is:
An hydrophobic amino acid selected from Alanine (Ala, A), Valine (Val, V), Methionine (Met, M), Leucine (Leu, L), Isoleucine (Ile, I), Phenylalanine (Phe, F), Proline (Pro, P) and analogues and derivatives thereof;
A basic amino acid selected from Arginine (Arg, R), Lysine (Lys, K) and Histidine (His, H) and analogues and derivatives thereof; or
Glycine (Gly, G) or Serine (Ser, S);
At the N terminal end of the peptide, X is selected from H, —CO—$R_1$ and —SO$_2$—$R_1$;
At the C terminal end of the peptide, Y is selected from OH, O$R_1$, NH$_2$, NH$R_1$ or N$R_1R_2$,
$R_1$ and $R_2$ being independently from each other, selected from an alkyle, aryle, aralkyle, alkylaryl, alkoxy and aryloxy group, that can be linear, branched, cyclic, poly-cyclic, non-saturated, hydroxylated, carbonylated, phosphorylated and/or sulphured, with the possibility to have in said group skeleton a 0, S and/or N heteroatom;

Pro* corresponding to a Proline, an analogue or derivative thereof;

Excluding the peptides where X=H and Y=OH.

According to the invention, as mentioned above, preferably in formula I:

Pro* is Proline, a natural amino acid; and/or $Xaa_1$ is selected from Alanine (Ala, A), Methionine (Met, M), Leucine (Leu, L), Isoleucine (Ile, I), Proline (Pro, P), Serine (Ser, S), Tyrosine (Tyr, Y) and Glutamine (Gln, Q); and more preferably selected from Leucine (Leu, L), Proline (Pro, P), Serine (Ser, S) and Glutamine (Gln, Q), and/or $Xaa_2$ is selected from Alanine (Ala, A), Arginine (Arg, R), Methionine (Met, M), Glycine (Gly, G) and Serine (Ser, S).

As mentioned above also, preferably the new tri-peptides according to the invention are selected from X-APA-Y, X-APR-Y, X-APM-Y, X-APG-Y, X-APS-Y, X-MPA-Y, X-MPR-Y, X-MPM-Y, X-MPG-Y, X-MPS-Y, X-LPA-Y, X-LPR-Y, X-LPM-Y, X-LPG-Y, X-LPS-Y, X-IPA-Y, X-IPR-Y, X-IPM-Y, X-IPG-Y, X-IPS-Y, X-PPA-Y, X-PPR-Y, X-PPM-Y, X-PPG-Y, X-PPS-Y, X-SPA-Y, X-SPR-Y, X-SPM-Y, X-SPG-Y, X-SPS-Y, X-YPA-Y, X-YPR-Y, X-YPM-Y, X-YPG-Y, X-YPS-Y, X-QPA-Y, X-QPR-Y, X-QPM-Y, X-QPG-Y, X-QPS-Y, X-GPA-Y, X-GPR-Y, X-GPM-Y, X-GPG-Y and X-GPS-Y, and more preferably X-LPA-Y, X-LPR-Y, X-LPM-Y, X-LPG-Y, X-LPS-Y, X-PPA-Y, X-PPR-Y, X-PPM-Y, X-PPG-Y, X-PPS-Y, X-SPA-Y, X-SPR-Y, X-SPM-Y, X-SPG-Y, X-SPS-Y, X-QPA-Y, X-QPR-Y, X-QPM-Y, X-QPG-Y and X-QPS-Y, and even more preferably X-SPR-Y, X-PPR-Y, X-QPA-Y, X-LPA-Y and X-SPA-Y when a dual activity pro-pigmenting and pro-collagen is seeked.

The preferred tetrapeptides according to the invention are X-AQPR-Y (SEQ ID NO: 1) and X-AQPK-Y (SEQ ID NO: 2).

According to other preferred features of the invention:

$R_1$ and/or $R_2$ is an alkyl chain having 1 to 24 carbon atoms, preferably 3 to 24 carbon atoms; and/or X is a CO—$R_1$ acyl group and Y is selected from OH, OMe, OEt and $NH_2$, preferably OH; X is preferably selected from octanoyl ($C_8$), decanoyl ($C_{10}$), lauroyl ($C_{12}$), myristoyl ($C_{14}$), palmitoyl ($C_{16}$), stearoyl ($C_{18}$), biotinoyl, elaidoyl, oleoyl and lipoyl; more preferably selected from lauroyl ($C_{12}$), myristoyl ($C_{14}$) and palmitoyl ($C_{16}$); and/or Y is OH and X is selected from palmitoyl ($C_{16}$), myristoyl ($C_{14}$) and lauroyl ($C_{12}$).

Preferably the peptide for the pro-pigmenting use according to the invention is selected from Pal-QPR-OH, Pal-YPR-OH, Pal-SPR-OH, Pal-LPR-OH, Myr-LPR-OH, Lau-LPR-OH, Pal-APR-OH, Pal-PPR-OH, Pal-QPK-$NH_2$, Pal-QPH-OH, Pal-QPM-OH, Pal-QPA-OH, Pal-LPA-OH, Pal-SPA-OH, Pal-PPA-OH, Myr-SPA-OH, Pal-LPM-OH, Pal-IPM-OH, Pal-MPL-OH, Pal-PR-OH, Myr-PR-OH, Pal-PM-OH, Pal-PP-OH, Pal-PG-OH, Pal-PS-OH, Pal-PA-OH, Pal-AP-OH and Pal-GP-OH.

Preferably for a dual activity pro-pigmenting and pro-collagen, the peptide is preferably selected from Pal-SPR-OH, Pal-PPR-OH, Pal-QPA-OH, Pal-LPA-OH, Myr-SPA-OH, Pal-PM-OH, and Pal-PA-OH.

The peptides of the invention may be optically pure, or consist of D or L isomers or a mixture thereof. The L isomers that are those found in nature may be preferred.

The peptides may be in the form of salts, especially hydrochloride salt.

In addition, the peptides of the invention may consist of a larger peptide fragment, containing more amino acids than the di-, tri-or tetra-peptide active "heart" of the invention.

The present invention also encompasses derivatives (with modification and/or addition of a chemical function but without change in the carbon skeleton) and analogues (with modification and/or addition of a chemical functional but with an additional change in the carbon skeleton), complex with other species such as a metal ion (eg copper, zinc, manganese, magnesium, and others).

Example of analogues of hydrophobic amino-acids for $Xaa_1$ and/or $Xaa_2$ can be for example for alanine the beta-alanine, alpha or gamma aminobutyric acid or 5-amino-valeric acid, as well as their superior homologues, the preferred one being the beta-alanine for alanine.

The present invention also provides a composition, especially topical, comprising at least one peptide according to the invention or according to the use of the invention in a physiologically acceptable medium. According to the excipient and the dosage of peptide, this composition will constitute for example a concentrated active ingredient or a less concentrated final composition directly for the patient.

"Physiologically acceptable medium" means according to the present invention, without limitation, an aqueous or hydroalcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hair and body hair), scalp and skin of mammals, particularly human, compositions which may be ingested or injected into the skin, without risk of toxicity, incompatibility, instability, allergic response, and others.

This "physiologically acceptable medium" forms what is commonly called the excipient of the composition.

The peptides of the invention may be dissolved in a lipophilic or hydrophilic matrix with a solubilizer if necessary according to future use.

The peptide(s) may be combined with other active ingredients in effective concentrations to act synergistically or to reinforce and to achieve the desired effects described in the invention, such as the following ingredients: radiation filters, including UVA UVB, moisturizing, calming, muscle relaxant, slimming, restructuring, firming, re-filling, firming, acting on the microcirculation, acting on inflammation, on free radicals, vitamins, anti-wrinkle agents, etc.

The peptide composition according to the invention can be applied to the face, body, neck, scalp, hair, eyelashes, body hair, in any form or vehicles known from the ones skilled in the art, in particular in the form of solution, dispersion, emulsion, paste or powder, individually or as a premix in vectors such as macrocapsules, microcapsules or nanocapsules, macrospheres, microspheres or nanospheres, liposomes, oleosomes or chylomicrons, macroparticles, microparticles or nanoparticles, macrosponges, microsponges or nanosponges, microemulsions or nanoemulsions, or adsorbed on organic polymer powders, talcs, bentonites, spores or exines and other inorganic or organic supports.

In particular in cosmetics, applications can be proposed including in the ranges of skin care for face, body, hair and body hair and makeup-care lines, including eyebrows and eyelashes.

The peptides according to the present invention may in general be used in any form whatsoever, in a form bound to or incorporated in or absorbed in or adsorbed on macro-, micro-, and nanoparticles, or macro-, micro-, and nanocapsules, for the treatment of textiles, natural or synthetic fibers, wools, and any materials that may be used for clothing or underwear for day or night intended to come into contact with the skin, handkerchiefs or cloths, to exert their cosmetic or therapeutical effect via this skin/textile contact and to permit continuous topical delivery.

The CTFA International cosmetic ingredient dictionary & handbook (13th Ed. 2010) (published by the Cosmetic, Toiletry, and Fragrance Combination, Inc., Washington, D.C.) describes a non-limited wide variety of cosmetic and pharmaceutical ingredients conventionally used in the skin care industry that can be used as additional ingredients/compounds in the compositions of the present invention.

Further skin care and hair care active ingredients that are particularly useful can be found in Sederma's commercial literature and on the website www.sederma.fr.

The following commercial actives can also be mentioned, as examples: betain, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (trade name of the acetyl hexapeptide-3 of Lipotec), spilanthol or an extract of Acmella oleracea known under the name Gatuline Expression™, an extract of Boswellia serrata known under the name Boswellin™, Deepaline PVB™ (Seppic), Syn-AKE™ (Pentapharm), Ameliox™ Bioxilift™ (Silab), PhytoCellTec™Argan (Mibelle), Papilactyl D™ (Silab), Preventhelia™ (Lipotec), Subliskin™ (Sederma), Venuceane™ (Sederma), Moist 24™ (Sederma), Vegesome Moist 24™ (Sederma), Essenskin™ (Sederma), Juvinity™ (Sederma), Revidrate™ (Sederma), Resistem™ (Sederma), Chronodyn™ (Sederma), Kombuchka™ (Sederma), Chromocare™ (Sederma), Calmosensine™ (Sederma), Glycokin factor S™ (Sederma), Biobustyl™ (Sederma), Idealift™ (Sederma), Ceramide 2™, Ceramide A2™ et Ceramide HO3™ (Sederma), Legance™ (Sederma), Intenslim™ (Sederma), Prodizia™ (Sederma), Beautifeye™ (Sederma), or mixtures thereof.

Among the plant extracts which can be combined with the peptide of the invention, there may more particularly be mentioned extracts of Ivy, in particular English Ivy (*Hedera helix*), of *Bupleurum chinensis*, of *Bupleurum falcatum*, of arnica (*Arnica montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum perforatum*), of butcher's-broom (*Ruscus aculeatus* L), of European meadowsweet (*Filipendula ulmaria* L), of big-flowered Jarva tea (*Orthosiphon stamincus benth*), of algae (*Fucus vesiculosus*), of birch (*Betula alba*), of green tea, of cola nuts (*Cola nipida*), of horse-chestnut, of bamboo, of *Centella asiatica*, of heather, of fucus, of willow, of mouse-ear, of escine, of cangzhu, of *Chrysanthellum indicum*, of the plants of the *Armeniacea* genus, *Atractylodis platicodon, Sinnomenum, Pharbitidis, Flemingia*, of *Coleus* such as *C. forskohlii, C. blumei, C. esquirolii, C. scutellaroides, C. xanthantus* and *C. barbatus*, such as the extract of root of *Coleus barbatus*, extracts of *Ballote*, of *Guioa*, of *Davallia*, of *Terminalia*, of *Barringtonia*, of *Trema*, of *antirobia, cecropia, argania, dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi, Aloe vera*, plant containing sterols (e.g., phytosterol), Manjistha (extracted from plants of the genus *Rubia*, particularly *Rubia cordifolia*), and Guggal (extracted from plants of the genus *Commiphora*, particularly *Commiphora mukul*), kola extract, chamomile, red clover extract, *Piper methysticum* extract (Kava Kava™ from SEDERMA), *Bacopa monieri* extract (Bacocalmine™ from SEDERMA) and sea whip extract, extracts of *Glycyrrhiza glabra*, of mulberry, of *melaleuca* (tea tree), of *Larrea divaricata*, of *Rabdosia rubescens*, of *Euglena gracilis*, of *Fibraurea recisa hirudinea*, of *Chaparral sorghum*, of sun flower extract, of *Enantia chlorantha*, of *Mitracarpe* of *Spermacocea* genus, of *Buchu barosma*, of *Lawsonia inermis* L., of *Adiantium capillus-veneris* L., of *Chelidonium majus*, of *Luffa cylindrica*, of Japanese Mandarin (*Citrus reticulata blanco* var. *unshiu*), of *Camelia sinensis*, of *Imperata cylindrica*, of *Glaucium flavum*, of *Cupressus sempervirens*, of *Polygonatum multiflorum*, of *Loveyly hemsleya*, of *Sambucus nigra*, of *Phaseolus lunatus*, of *Centaurium*, of *Macrocystis pyrifera*, of *Turnera diffusa*, of *Anemarrhena asphodeloides*, of *Portulaca pilosa*, of *Humulus lupulus*, of *Coffea arabica*, of *Ilex paraguariensis*, of *Globularia cordifolia*, of *Albizzia julibrissin, Oxydendron arboretum* or of *Zingimber zerumbet* Smith.

The compositions of the present invention may include other peptides, including, without limitation, the di-, tri-, tetra-, penta-and hexapeptides and their derivatives. According to a particular embodiment, the concentration of the additional peptide, in the composition, ranges from $1 \times 10^{-7}\%$ and 20%, preferably from $1 \times 10^{-6}\%$ and 10%, preferably between $1 \times 10^{-5}\%$ and 5%, by weight.

According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides which are found in nature, and/or are commercially available.

Suitable dipeptides for use within the scope of the present invention include but are not limited to carnosine (beta-AH), YR, VW, NF, DF, KT, KC, CK, KP, KK or TT. Non limitative suitable tripeptides for use herein include, but are not limited to RKR, HGG, GHK, GKH, GGH, GHG, KFK, KPK, KMOK, KMO₂K or KAvaK. Non limitative suitable tetrapeptides for use herein include but are not limited to RSRK (SEQ ID NO: 3), GQPR (SEQ ID NO: 4) or KTFK (SEQ ID NO: 5). Non limitative suitable pentapeptides include, but are not limited to KTTKS (SEQ ID NO: 6) and hexapeptides include but are not limited to GKTTKS (SEQ ID NO: 7) and VGVAPG (SEQ ID NO: 8).

Other suitable peptides for use in the context of the present invention include, but are not limited to: lipophilic derivatives of peptides, preferably palmitoyl derivatives, and metal complexes as aforementioned (e.g. copper complex of the tripeptide HGG). Preferred dipeptide derivatives include N-Palmitoyl-beta-Ala-His, N-Acetyl-Tyr-Arg-hexadecylester (Calmosensine™, Idealift™ from Sederma). Preferred tripeptide derivatives include in particular the N-Palmitoyl-Gly-Lys-His, and Pal-Gly-His-Ly, (Pal-GKH and Pal-GHK from Sederma), the copper derivative of HGG (Lamin™ from Sigma), Lipospondin (N-Elaidoyl-KFK) and its analogues of conservative substitution, N-Acetyl-RKR-NH₂ (Peptide CK+), N-Biot-GHK (from Sederma), Pal-KMO₂K (Sederma) and derivatives thereof. Suitable tetrapeptide derivatives for use according to the present invention include, but are not limited to, N-palmitoyl-GQPR (SEQ ID NO: 9) (from Sederma), Ela-KTFK (SEQ ID NO: 10). Suitable pentapeptide derivatives for use herein include, but are not limited to, N-Palmitoyl-KTTKS (SEQ ID NO: 11) (available as Matrixyl™ from Sederma), N-Palmitoyl-Tyr-Gly-Gly-Phe-X (SEQ ID NO: 12) with X Met or Leu or mixtures thereof. Suitable hexapeptide derivatives for use herein include, but are not limited to, N-Palmitoyl-VGVAPG (SEQ ID NO: 13), Pal-GKTTKS (SEQ ID NO: 14) and derivatives thereof. The mixture of Pal-GHK and Pal-GQPR (SEQ ID NO: 9) (Matrixyl™ 3000, Sederma) can also be mentioned.

The preferred compositions commercially available containing a tripeptide or a derivative include Biopeptide-CL™, Maxilip™, Biobustyl™, Procapil™ and Matrixyl™synthe'6™ of Sederma. The compositions commercially available preferred sources of tetrapeptides include Rigin™, Eyeliss™, Matrixyl™ Reloaded and Matrixyl 3000™ which contain between 50 and 500 ppm of Palmitoyl-GQPR (SEQ ID NO: 9) and carrier, proposed by Sederma.

The following marketed peptides can be mentioned as well as additional active ingredients: Vialox™, Syn-ake™ or Syn-Coll™ (Pentapharm), Hydroxyprolisilane CN™ (Exsymol), Argireline™, Leuphasyl™, Aldenine™, Trylgen™, Eyeseryl™, Serilesine™ or Decorinyl™ (Lipotec), Collaxyl™ or Quintescine™ (Vincience), BONT-L-Peptide™ (Infinitec Activos), Cytokinol™LS (Laboratoires Serobiologiques/Cognis), Kollaren™ IP2000™ or Melip-rene™ (Institut Européen de Biologie Cellulaire), Neutrazen™ (Innovations), ECM-Protect™ (Atrium Innovations), Timp-Peptide™ or ECM Moduline™ (Infinitec Activos).

The present invention also provides a topical cosmetic, cosmeceutical or dermopharmaceutical treatment method to improve the appearance and condition of the skin and its appendages, comprising the topical application to the skin of a subject in need thereof of an effective amount of a peptide according to the invention or a composition according to the invention comprising said peptide as recited above.

"Topical treatment" or "topical use" means an application that is intended to act where it is applied: skin, mucous, appendages.

The peptide or composition according to the invention can be applied locally applied to targeted areas.

The "effective" amount depends on various factors, such as the age, the condition of the patient, the severity of the disorder or disease and the administration mode. An effective amount means a non-toxic amount enough to achieve the desired effect.

In a cosmetic composition according to the invention, the peptides to be present in an effective amount, are generally present in an amount ranging from 0.000001% and 15% based on the total weight of the composition, preferably between 0.0001% and 5% depending on the destination of the composition and the more or less pronounced derised effect. The peptides may be present in the compositions according to the invention in varying relative proportions, in equivalent amounts or otherwise in different proportions.

All percentages and ratios used herein are by weight of the total composition and all measurements are made at 25° C. unless it is otherwise specified.

For example, for a face cosmetic treatment, the SCCCS'S (Scientific Committee on Consumer Safety) Notes of Guidance for the testing of cosmetic substances and their safety evaluation ($8^{th}$ Revision, 11 Dec. 2012) has set a standard amount for applying a cream of 2.72 $mg/cm^2$/day/person and for a body lotion of 0.5 $mg/cm^2$/day/person.

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a composition comprising the peptide of the invention, and in a second compartment an excipient and/or an additional active, the compositions contained in the said first and second compartments in this case being considered to be a combination composition for simultaneous, separate or stepwise use in time, particularly in one of the treatment methods recited above.

The treatment method according to the invention is particularly suitable for:

A pro-pigmenting treatment;

To prevent and/or treat the loss of pigmentation of the skin and its appendages (body hair, eyelashes, eyebrows or hair), especially for treating cutaneous white spots and/or canities;

To improve cutaneous phototype of a person with a white and/or sensitive skin in particular to prepare the skin and its appendages to sun exposure;

A tanning, tanning accelerating treatment;

To prevent and/or treat the default of complexion homogeneity;

For preventing and/or treating the loss of collagen in the skin extracellular matrix or for stimulating the synthesis of collagen to obtain a volumizing effect;

For preventing and/or treating the loss of skin hydration by improving the skin barrier and/or;

For an anti-aging treatment, in particular anti-wrinkles and fine lines, moisturizing and for unifying.

Other applications can be envisaged for example slimming, loss of elasticity, detoxification, anti-glycation, anti-free radical, anti-oxidants, tensor, anti-fatigue, anti-dark circles and/or under eye rings, calming, firming, hair and body hair growth, complexion etc. for a preventive or curative action.

DETAILED DESCRIPTION

The following examples describe and illustrate some aspects of the invention. They should not be seen as limiting the disclosure, as they only provide useful information for understanding and implementation.

A) Example of Synthesis of the Peptide According to the Invention, the Pal-PA-OH:

The Pal-PA-OH peptide is prepared by peptidic synthesis. Proline is acylated on its amine function with an activated derivative of palmitic acid (palmitoyl chloride for example) in the presence of a base to obtain the palmitoyl-proline. The latter is then activated on its terminal acid function with a coupling agent (DCC (diclyclohexylcarbodiimide)/NHS (N-hydroxysuccinimide) or HBTU (2-1H-enzotriazole-1-yl)-1,1,3,3-tetramethyluronium hexafluorophosphate)/HOBT (1-hydroxybenzotriazole)) to react with the alanine. After precipitation, washing and drying, the palmitoyl-prolyl-alanine product is obtained in a solid form.

B) Preparation of a Composition According to the Invention Comprising the Pal-PA-OH Peptide of Example A).

Starting Products:

The Pal-PA-OH pur peptide, synthetized according the synthesis method explained above;

Excipient: a mixture of fatty esters, selected to form an oil matrix, for example for forming a water-free composition for the formulation of subsequent cosmetic water-free end-compositions.

Protocol:

the Pal-PA-OH peptide is mixed with the excipient and placed under gentle stirring and heating until complete dissolution and clarity.

C) In Vitro Evaluations

The peptides of the invention have a number of remarkable effects presented below. Peptides prepared according to A) above and dissolved in a fatty excipient to form compositions according to Example B) were in vitro tested and demonstrated a pro-pigmenting activity and for some of them an additional pro-collagen activity, that are presented below. Comparative tests are also presented below.

1. Pro-Pigmenting Activity (Melanogenesis)

a) Test on B16 Cells

Mouse melanoma (B16 cells) were grown in their maintenance medium (DMEMc+10% FCS) in the presence of the products and positive references from the literature for 48 hours. At the end of the contact, the melanins were extracted from the cells and assayed by spectrophotometry. In parallel, the residual tyrosinase activity (dopa oxidase) of the cells was assayed by spectrophotometry in the presence of one of the substrates of the enzyme: the L-DOPA. An estimate of the viability of the cells was also performed at the end of culture using a protein assay by the BCA method.

b) Test on Human Melanocytes

Normal human melanocytes (HEMn cells) were seeded in their maintenance medium then brought into contact with the products and the positive controls (literature references) in a test medium suitable for the culture of melanocytes for 10 days. At the end of the contact, the melanin are extracted from cells and assayed by spectrophotometry. In parallel, the residual tyrosinase activity (dopa oxidase) of the cells was assayed by spectrophotometry in the presence of one of the substrates of the enzyme: the L-DOPA. An estimate of the viability of the cells was also performed at the end of culture using a protein assay by the BCA method.

c) Results on Pro-Pigmentation

| Peptides | On B16 cells | On human melanocytes |
|---|---|---|
| IBMX (isobutyl-methyl-xanthine) | +++ | +++ |
| Pal-AQPR-OH (SEQ ID NO: 15) | +++ | |
| Pal-AQPK-OH (SEQ ID NO: 16) | +++ | |
| Pal-QPR-OH | ++ | |
| Pal-YPR-OH | ++++ | ++ |
| Pal-SPR-OH | ++++ | ++ |
| Pal-LPR-OH | ++++ | +++ |
| Myr-LPR-OH | | ++ |
| Lau-LPR-OH | | +++ |
| H-LPR-OH | | =0 |
| Pal-APR-OH | +++ | |
| Pal-PPR-OH | +++ | ++ |
| Pal-QPK-NH₂ | ++ | |
| Pal-QPH-OH | +++ | |
| Pal-QPM-OH | +++ | |
| Pal-QPA-OH | +++ | ++ |
| Pal-LPA-OH | + | ++ |
| Myr-DPA-OH | | =0 |
| Pal-SPA-OH | | ++ |
| Pal-PPA-OH | | + |
| Pal-DPA-OH | | =0 |
| Myr-SPA-OH | | ++ |
| Pal-LGA-OH | | =0 |
| Pal-LPM-OH | + | |
| Pal-IPM-OH | + | |
| Pal-MPL-OH | +++ | |
| Pal-PR-OH | +++ | + |
| Myr-PR-OH | | + |
| Pal-PM-OH | +++ | + |
| Pal-PP-OH | | +++ |
| Pal-PG-OH | | +++ |
| Pal-PS-OH | | ++ |
| Pal-PA-OH | | +++ |
| H-PA-OH | | =0 |
| Pal-GA-OH | | =0 |
| Pal-AP-OH | | ++ |
| Pal-GP-OH | | + |

The results show a more or less pro-pigmenting activity for a representative panel of peptides according to the invention.

The Table Gives Also Comparative Results:

The Pal-LGA-OH and Pal-GA-OH show no pro-pigmenting activity compared to Pal-LPA-OH and Pal-PA-OH showing that when Proline is substitute by a more flexible amino acid, here glycine, it annihilates the pro-pigmenting activity.

It can also be seen that Myr-DPA-OH and Pal-DPA-OH, including an acid $Xaa_1$ (Asp (D) aspartic acid) do not present either a pro-pigmenting activity.

Furthermore, Pal-FPM-OH, with a nonpolar $Xaa_1$ (Phenylalanine Phe (F)) does not present either a pro-pigmenting activity.

Finally, H-LPR-OH and H-PA-OH have no pro-pigmenting activity unlike Pal-LPR and Pal-PA-OH respectively, which shows the importance of having peptides with a substitution at X or Y.

2. Pro-Pigmenting and Pro-Collagen Dual Activity

Normal human fibroblasts are seeded and placed in contact with the peptides to test for 6 days in DMEMc+5% FCS. After the contact, the layers are fixed and collagen 1 fibers are visualized by immunostaining with a specific antibody. Quantification is then performed by image analysis. The positive control is TGF β $10^{-6}$%.

| Peptide | Melanogenesis on B16 cells | Melanogenesis on human melanocytes | Coll 1 |
|---|---|---|---|
| Pal-SPR-OH | ++++ | ++ | + |
| Pal-PPR-OH | +++ | | + |
| Pal-QPA-OH | +++ | ++ | + |
| Pal-LPA-OH | + | ++ | +++ |
| Myr-SPA-OH | | ++ | ++ |
| Pal-PM-OH | +++ | + | ++ |
| Pal-PA-OH | | +++ | ++ |

3. Activity on Keratinocytes

Human keratinocytes are brought to just confluence in KSFMc environment. The contact with the actives and therefore their evaluation is then done in KSFMc medium alone or with calcium (0.8 mm)*. Visual evaluation of differentiation takes place after 2, 4/5 and 7 days of contact.

*Calcium differentiation allows the creation of link structure between the cells which leads to a better attachment of the basal layers.

| Peptide | Keratinocyte differenciation |
|---|---|
| Pal-KT - positive control | +++ at 2.5 ppm |
| Pal-LPR | + at 10 ppm |
| Pal-SPR | + at 10 ppm |
| Pal-PA | + at 2 ppm |
| Pal-LPA | ++ at 3 ppm |

D) Galenics

Active Ingredient According to the Invention:

Formulas comprising a peptide of the invention either is in a hydrophobic excipient as in the previous examples or in a hydrophilic excipient.

Different formulations are described below. Additional cosmetic active ingredients, in support and/or in complement of the activity of the active ingredient according to the invention if necessary can be added to the appropriate phase according to their hydrophobic or hydrophilic nature. These ingredients can be of any class according to their(s) function(s), place of application (body, face, neck, chest, hands, hair, eyelashes, eyebrows, body hair, etc.), final desired effect and target consumer, for example anti-aging, anti-wrinkle, moisturizing, anti-wrinkle, firming, anti-glycation, slimming, soothing, myo-relaxing, anti-redness, anti-stretch marks, etc. They are mentioned above in the text.

1) Cream Form

| Ingredient (INCI name) | Weight % |
| --- | --- |
| Phase A | |
| Sorbitan Stearate | 3.00 |
| Cyclopentasiloxane (and) Cyclohexasiloxane | 2.00 |
| Ethylhexyl Palmitate | 3.00 |
| Glyceryl Stearate (and) PEG-100 Stearate | 3.00 |
| Ethylhexyl Methoxycinnamate | 1.00 |
| Ethylhexyl Dimethyl PABA | 1.00 |
| Phase B | |
| Demineralised water | Qsp 100 |
| Ultrez 10 ™ (Carbomer) | 0.40 |
| Phase C | |
| Glycerin | 5.00 |
| Conservatives | qs |
| Phase D | |
| Peptide according to the invention in a fatty excipient | 2.00 |
| Phase E | |
| Potassium sorbate (Potassium Sorbate) | 0.10 |
| Phase F | |
| Sodium hydroxyde 30% (Sodium Hydroxide) | 0.60 |
| Demineralised water | 6.00 |
| Phase G | |
| Fragrance | 0.10 |

Protocol:

Weigh phase A and heat to 75° C. in a water bath. Weigh phase B and let swell for 20 minutes. Melt phase C until dissolved and add to phase B. Heat phase (B+C) to 75° C. in a water bath. Pour phase A in phase (B+C) under stirring. Extemporaneously, add phase A to phase (A+B+C). Approximately at 45° C. add phase E and neutralize with phase F. Mix well. At 35° C., add phase G. Homogenize well. pH: 6.20.

Examples of Ingredients that can be Added to this Formulation:

CALMOSENSINE™: soothing active for sensitive skins marketed by Sederma (W1998/07744) comprising the Tyr-Arg lipo-dipeptide. It reduces discomfort feelings.

NG Birch Sap™: skin toning and moisturizing marketed by Sederma.

Shea Butter: having nourishing and protective properties for the treatment of skin stressed by the environment.

2) Oil Form, in Particular for a Spray

| Ingredient (INCI name) | Weight % |
| --- | --- |
| Phase A | |
| Crodamol GTCC ™ (Capric/Caprylic Triglyceride) | Qsp 100 |
| Ethylhexyl Dimethyl PABA | 2.00 |
| Ethylhexyl Methoxycinnamate | 2.00 |
| Crodamol OS ™ (Ethylhexyl Stearate) | 20.00 |
| Tocopherol Acetate | 0.20 |
| Phase B | |
| Peptide according to the invention in a fatty excipient | 2.00 |
| Phase C | |
| Fragrance | 0.05 |

Protocol:

Weigh phase A and put under helix stirring. Add phase B to phase A under helix stirring. Mix well. Add phase C to phase (A+B).

Examples of Ingredients that can be Added to this Formulation:

REVIDRATE™: active marketed by Sederma (WO2011/086532) that in particular improves the cohesion of the epidermis and its hydration.

RENOVAGE™: global anti-aging active ingredient marketed by Sederma (WO2006/120646).

Gel Form

| Ingredient (INCI name) | Weight % |
| --- | --- |
| Phase A | |
| Demineralised water | Qsp 100 |
| Ultrez 10 ™ (Carbomer) | 0.20 |
| Phase B | |
| PEG 400 ™ | 5.00 |
| Conservatives | qs |
| Phase C | |
| Dimethicone | 4.00 |
| Pemulen TR2 ™ (Acrylates/C10-30 Alkyl Acrylate Cross Polymer) | 0.20 |
| Phase D | |
| Tween 20 ™ (Polysorbate 20) | 1.00 |
| Peptide according to the invention in a fatty excipient | 2.00 |
| Phase E | |
| Potassium sorbate (Potassium Sorbate) | 0.10 |
| Phase F | |
| Sodium hydroxyde 30% (Sodium Hydroxide) | 0.60 |
| Demineralised water | 5.00 |
| Phase G | |
| Fragrance | 0.10 |

Protocol:

Disperse Ultrez 10 in water and let swell for 15 minutes. Heat phase B until dissolved and add to phase A. Weigh and mix phase C. Mix phase D and add it to phase C; mix well. Add phase (C+D) to the phase (A+B). Then add phase E. Let swell for 1 hour. Mix well. Neutralize with phase F. Finally, add phase G. pH: 6.10.

Examples of Ingredients that can be Added to this Formulation:

RESISTEM™: anti-aging marketed by Sederma (WO2012/104774), helping the skin to build its own anti-aging defense system, based on an extract obtained by cell culture of *Globularia cordifolia* plant.

AQUALANCE™: osmoprotector moisturising active ingredient marketed by Sederma (WO2009/104118) comprising homarine and erythritol.

LEGANCE™: anti-aging active marketed by Sederma (WO2013/105047), corresponding to a *Zingiber zerumbet* Smith extract obtained by $C_{O2}$ supercritical in a water-soluble excipient and titrated in zerumbone ingredient. It is a global anti-aging ingredient for legs. It improves their appearance and comfort by reducing water retention, improving microcirculation and refining adipose tissue.

BODYFIT™: slimming/firming active ingredient comprising glaucine marketed by Sederma (WO2004/024695). BODYFIT™ reduces the appearance of cellulite and helps to improve drainage and water distribution in the tissues.

PRODIZIA™: active ingredient marketed by Sederma (WO2013/046137) fighting the signs cutaneous fatigue caused by glycation and glycoxidation.

JUVINITY™: active (WO2011/125039) marketed by Sederma reducing signs of aging on the face and neckline, smoothing wrinkles, densifying and restructuring the dermis.

Compact Powder Form

| Ingredient (INCI name) | Weight % |
|---|---|
| Phase A | |
| Talc | Qsp 100 |
| Kaolin | 2.00 |
| Calcium Stearate | 1.00 |
| Mica | 4.00 |
| Silica | 1.00 |
| Bismuth Oxychloride | 2.00 |
| Potassium Sorbate | qs |
| Phenoxyethanol | qs |
| Phase B | |
| Unipure ™ Black LC 989 HLC [CI 77499 (and) Hydrogenated Lecithin] | 0.20 |
| Unipure ™ Red LC 381 HLC [CI 77491 (and) Hydrogenated Lecithin] | 0.60 |
| Unipure ™ Yellow LC 182 HLC [CI 77492 (and) Hydrogenated Lecithin] | 1.00 |
| Covapearl Star ™ Gold 2302 AS [CI 77891 (and) CI 77491 (and) Synthetic Fluorphlogopite (and) Triethoxycaprylylsilane] | 0.50 |
| Covapearl ™ Brown 838 HLC [CI 77491 (and) Mica (and) Hydrogenated Lecithin] | 1.00 |
| Covapearl ™ Dark Blue 637 [CI 77510 (&) CI 77891 (&) Mica] | 0.10 |
| Phase C | |
| Crodamol PTIS-LQ-(MV) ™ [Pentaerythrityl Tetraisostearate] | 4.00 |
| Peptide according to the invention in a fatty matrix | 2.00 |
| Phase D | |
| Fragrance | 0.30 |

Protocol:

Weigh phase A and mix. Weigh phase B and pour into phase B. Pour (A+B) in the blender and mix. Add phase C to (A+B) in several times and mix each time. Add phase D. Check homogeneity at each step.

Examples of ingredients that can be added to this formulation:

VEGESOME MOIST 24™: ingredient marketed by Sederma designed for the formulation of moisturizing powder makeup; it is a powder consisting of hollow particles 25 microns (*Lycopodium clavatum* exins) loaded with an *Imperata cylindrica* extract having moisturizing properties.

Other Cream Form

| Ingredient (INCI name) | Weight % |
|---|---|
| Phase A | |
| Arlacel 170 ™ (Glyceryl Stearate (and) PEG-100 Stearate) | 5.50 |
| Abil Wax 2434 ™ (Stearoxy Dimethicone) | 3.00 |
| Acetulan ™ (Cetyl Acetate (and) Acetylated Lanolin Alcohol) | 1.50 |
| Crodacol C 90 ™ (Cetyl Alcohol) | 1.50 |
| Mineral Oil | 3.00 |
| Shea Butter | 5.00 |
| Unsaponifiable Shea | 1.00 |
| Parsol MCX ™ (Ethylhexyl Methoxicinnamate) | 3.50 |
| Phase B | |
| Demineralised water | Qs 100 |
| Phase C | |
| Carbopol 940 ™ (Carbomer) | 0.20 |
| Phase D | |
| Demineralised water | 2.00 |
| Triethanolamine 99% (Triethanolamine) | 0.20 |
| Phase E | |
| Propylene Glycol | 0.10 |
| Mixed Parabens | |
| Phase F | |
| Sodium hydroxyde 30% (Sodium Hydroxide) | 5.00 |
| Demineralised water | qs |
| Phase G | |
| Peptide according to the invention in an hydrophilic excipient | 2.00 |

Protocol:

Weigh phase A and heat at 75° C. in a water bath. Weigh phase B and let swell for 20 minutes. Melt phase C until dissolved and add it to phase B. Heat phase (B+C) at 75° C. in a water bath. Pour phase A in phase (B+C) under Staro stirring. Extemporaneously, add phase A to phase (A+B+C). At approximately 45° C. add phase E and neutralize with phase F. Mix well. At 35° C., add phase G. Homogenize well. pH: 6.20.

Examples of Ingredients that can be Added to this Formulation:

SUBLISKIN™: active ingredient marketed by Sederma (WO2010/067327) that moisturizes and smooths the skin while allowing it to resist to external aggressions.

VENUCEANE™: active marketed by Sederma (WO2002/066668) comprising a *Thermus* thermophiles biotechnological extract, that prevents visible signs of photo-aging (spots, wrinkles, dryness . . . ), protects cell structures from damages caused by UV and strengthens skin integrity.

MATRIXYL synthe'6™: peptide-based anti-wrinkle ingredient marketed by Sederma (WO2010/082175) which helps repair skin damage caused by aging.

KOMBUCHKA™: active ingredient acting on complexion marketed by Sederma (WO2004/012650).

INTENSLIM™: slimming active ingredient marketed by Sederma (WO2013/105048) which is a synergistic combination of extracts obtained by *Globularia cordifolia* plant cell culture, *Zingiber zerumbet* Smith titrated in zerumbone and vegetable caffeine obtained by supercritical $CO_2$ extraction.

Depigmenting Hair Lotion

| Ingredient (INCI name) | Weight % |
|---|---|
| Phase A | |
| Demineralised water | Qsp 100 |
| Ethanol | 50.00 |
| Phase B | |
| Methyl Paraben | 0.20 |
| Butylene Glycol | 2.00 |
| Phase C | |
| Tween 20 ™ [Polysorbate 20] | 1.50 |
| Fragrance | 0.10 |
| Phase D | |
| Peptide according to the invention | 3.00 |

Protocol:

Weigh phase A. Weigh and melt phase B. Cool phase B. Mix phase B with phase A under propeller stirring. Mix phase C and add to phase (A+B). Add phase D to phase (A+B+C). pH: 6.70.

Examples of Ingredients that can be Added to this Formulation:

PROCAPIL™: anti-hair-loss active ingredient marketed by Sederma (WO 00/58347) that combines a vitamin matrikine (biotinyl-GHK), apigenin (a flavonoid extracted from citrus) and oleanolic acid (root extract from *Loveyly hemsleya*).

The invention claimed is:

1. A dipeptide of formula (I):

$$X\text{-}(Xaa1)n\text{-}Pro^*\text{-}(Xaa2)m\text{-}Y \quad (I)$$

Wherein n=0 and m=1;

$Xaa_2$ is Alanine (Ala, A);

wherein at the N terminal end of the dipeptide of formula (I), X is selected from the group consisting of octanoyl ($C_8$), decanoyl ($C_{10}$), lauroyl ($C_{12}$), myristoyl ($C_{14}$), palmitoyl ($C_{16}$), stearoyl ($C_{18}$), biotinoyl, elaidoyl, oleoyl and lipoyl;

wherein at the C terminal end of the dipeptide of formula (I), Y is selected from the group consisting of OH, OR1, NH2, NHR1 and NR1R2;

wherein R1 and R2 are independent from each other and selected from the group consisting of an acyl, alkyl, aryl, aralkyl, alkylaryl, alkoxy and aryloxy group, wherein said acyl, alkyl, aryl, aralkyl, alkylaryl, alkoxy and aryloxy group can be linear, branched, cyclic, poly-cyclic, non-saturated, hydroxylated, carbonylated, phosphorylated and/or sulfured, and may include an O, S and/or N heteroatom;

wherein Pro* is Proline; and wherein the dipeptide of formula (I) does not include the dipeptide wherein X=H and Y=OH.

2. The dipeptide of formula (I) according to claim 1, wherein X is selected from the group consisting of lauroyl ($C_{12}$), myristoyl ($C_{14}$) and palmitoyl ($C_{16}$).

3. The dipeptide of formula (I) according to claim 2, wherein said dipeptide is Pal-PA-OH.

* * * * *